(12) United States Patent
Parker

(10) Patent No.: US 7,361,136 B2
(45) Date of Patent: Apr. 22, 2008

(54) METHOD AND APPARATUS FOR GENERATING A THERAPEUTIC MAGNETIC FIELD

(76) Inventor: Richard F. Parker, 6118 Dusenburg Rd., Delray Beach, FL (US) 33484

(*) Notice: Subject to any disclaimer, the term of this patent is extended or adjusted under 35 U.S.C. 154(b) by 0 days.

(21) Appl. No.: 11/139,109

(22) Filed: May 27, 2005

(65) Prior Publication Data

US 2005/0267355 A1    Dec. 1, 2005

Related U.S. Application Data

(60) Provisional application No. 60/574,735, filed on May 27, 2004.

(51) Int. Cl.
*A61N 1/00* (2006.01)

(52) U.S. Cl. ...................................... 600/14

(58) Field of Classification Search ............. 600/9–15, 600/407, 409, 411
See application file for complete search history.

(56) References Cited

U.S. PATENT DOCUMENTS

| | | |
|---|---|---|
| 703,989 A | 7/1902 | Burry |
| 3,658,051 A | 4/1972 | MacLean |
| 3,915,151 A | 10/1975 | Kraus |
| 4,066,065 A | 1/1978 | Kraus |
| 4,177,796 A | 12/1979 | Franco-Vila |
| 4,233,965 A | 11/1980 | Fairbanks |
| 4,266,532 A | 5/1981 | Ryaby et al. |
| 4,374,516 A | 2/1983 | Harrison |
| 4,398,545 A | 8/1983 | Wilson |
| 4,402,309 A | 9/1983 | Harrison |
| 4,428,366 A | 1/1984 | Findl et al. |
| 4,527,550 A | 7/1985 | Ruggera et al. |
| 4,537,181 A | 8/1985 | Shalhoob et al. |
| 4,641,633 A | 2/1987 | Delgado |
| 4,674,482 A | 6/1987 | Waltonen et al. |
| 4,693,238 A | 9/1987 | Jerabek |
| 4,757,804 A | 7/1988 | Griffith et al. |
| 4,758,429 A | 7/1988 | Gordon |
| 4,765,310 A | 8/1988 | Deagle et al. |
| 4,818,697 A | 4/1989 | Liboff et al. |
| 4,932,951 A | 6/1990 | Liboff et al. |
| 4,940,453 A | 7/1990 | Cadwell |
| 4,993,413 A | 2/1991 | McLeod et al. |
| 5,017,185 A | 5/1991 | Baermann |
| 5,045,050 A | 9/1991 | Liboff et al. |
| 5,059,298 A | 10/1991 | Liboff |
| 5,066,272 A | 11/1991 | Eaton et al. |

(Continued)

*Primary Examiner*—Samuel G Gilbert
(74) *Attorney, Agent, or Firm*—McHale & Slavin, P.A.

(57) ABSTRACT

An method for generating a therapeutic magnetic field to be applied to a biological subject is disclosed wherein biomagnetic fields are measured and component vector wave patterns are derived therefrom, and a therapeutic Normalizing Signal is derived from the harvested wave patterns. A therapeutic apparatus is provided which is operable to generate magnetic fields having a vector component wave pattern approximately equal to the Normalizing Signal. In a preferred embodiment, magnetic field measurements for a selected site are taken from Normal and Abnormal test subjects, and a Difference Wave is derived from the data. The Normalizing Signal can then be derived from the Difference Wave using predefined algorithms. The therapeutic apparatus has a coil which has known current/magnetic field characteristics so that source current can be calculated to generate a magnetic field which is a function of the Normalizing Signal.

31 Claims, 6 Drawing Sheets

U.S. PATENT DOCUMENTS

| | | | |
|---|---|---|---|
| 5,067,940 | A | 11/1991 | Liboff et al. |
| 5,077,934 | A | 1/1992 | Liboff et al. |
| 5,087,336 | A | 2/1992 | Liboff et al. |
| 5,088,976 | A | 2/1992 | Liboff et al. |
| 5,100,373 | A | 3/1992 | Liboff et al. |
| 5,106,361 | A | 4/1992 | Liboff et al. |
| 5,123,898 | A | 6/1992 | Liboff et al. |
| 5,143,588 | A | 9/1992 | Liboff et al. |
| 5,156,587 | A | 10/1992 | Montone |
| 5,160,591 | A | 11/1992 | Liboff et al. |
| 5,181,902 | A | 1/1993 | Erickson et al. |
| 5,183,456 | A | 2/1993 | Liboff et al. |
| 5,211,622 | A | 5/1993 | Liboff et al. |
| 5,215,633 | A | 6/1993 | Liboff et al. |
| 5,215,642 | A | 6/1993 | Liboff et al. |
| 5,267,939 | A | 12/1993 | Liboff et al. |
| 5,269,745 | A | 12/1993 | Liboff et al. |
| 5,290,409 | A | 3/1994 | Liboff et al. |
| D345,799 | S | 4/1994 | Lamond et al. |
| 5,314,400 | A | 5/1994 | Tsyb et al. |
| 5,315,994 | A | 5/1994 | Guibert et al. |
| 5,316,634 | A | 5/1994 | McLeod |
| 5,317,155 | A | 5/1994 | King |
| 5,318,561 | A | 6/1994 | McLeod et al. |
| 5,344,384 | A | 9/1994 | Ostrow et al. |
| 5,387,176 | A | 2/1995 | Markoll |
| 5,401,233 | A | 3/1995 | Erickson et al. |
| 5,441,528 | A | 8/1995 | Chang et al. |
| 5,443,487 | A | 8/1995 | Guibert et al. |
| 5,453,073 | A | 9/1995 | Markoll |
| 5,501,704 | A | 3/1996 | Chang et al. |
| 5,518,495 | A | 5/1996 | Kolt |
| 5,634,939 | A | 6/1997 | Kuster et al. |
| 5,665,049 | A | 9/1997 | Markoll |
| 5,669,868 | A | 9/1997 | Markoll |
| 5,697,883 | A | 12/1997 | Anninos et al. |
| 5,738,625 | A | 4/1998 | Gluck |
| 5,766,124 | A | 6/1998 | Polson |
| 5,792,040 | A | 8/1998 | Koeneman et al. |
| 5,880,661 | A | 3/1999 | Davidson et al. |
| 6,004,257 | A * | 12/1999 | Jacobson ............... 600/9 |
| 6,029,090 | A | 2/2000 | Herbst |
| 6,083,149 | A | 7/2000 | Wascher et al. |
| 6,149,577 | A | 11/2000 | Bouldin et al. |
| 6,213,933 | B1 | 4/2001 | Lin |
| 6,213,934 | B1 * | 4/2001 | Bianco et al. ............ 600/14 |
| 6,334,069 | B1 | 12/2001 | George et al. |
| 6,336,045 | B1 | 1/2002 | Brooks |
| 6,353,763 | B1 | 3/2002 | George et al. |
| 6,402,678 | B1 | 6/2002 | Fischell et al. |
| 6,418,345 | B1 | 7/2002 | Tepper et al. |
| 6,443,883 | B1 | 9/2002 | Ostrow et al. |
| 6,461,289 | B1 | 10/2002 | Muntermann |
| 6,527,695 | B1 | 3/2003 | Davey et al. |
| 6,561,968 | B1 | 5/2003 | Dissing et al. |
| 6,592,509 | B1 | 7/2003 | Hunter, Jr. |
| 6,681,131 | B2 | 1/2004 | Kandori et al. |
| 6,735,460 | B2 | 5/2004 | Tsukada et al. |

* cited by examiner

Normal component $B_z(t)$ of magnetic field of healthy/normal GI tract

Normal component $B_z(t)$ of magnetic field of abnormal GI tract

METHOD AND APPARATUS FOR GENERATING A THERAPEUTIC MAGNETIC FIELD

CROSS REFERENCE TO RELATED APPLICATIONS

This application claims the benefit of U.S. Provisional Application No. 60/574,735 filed May 27, 2004, the contents of which is hereby incorporated by reference.

FIELD OF THE INVENTION

The present invention relates generally to devices for promoting healing processes through the generation of localized magnetic fields, and more particularly to a method for capturing natural biologic waveforms in order to derive an electronic repair/normalizing signal suitable for treating a particular injury or disease state.

BACKGROUND OF THE INVENTION

Physiological processes generally involve complex chemical and physical processes which have an electrical aspect. These electrical-based processes generate specific and measurable minute magnetic fields which are a function of the electrical field. The basic complex magnetic field structures associated with natural physiological processes are representative of those processes. One of the natural physiological processes is the so-called "healing process," which is a complex make-up of all chemical and physical interactions as directed by the body's natural repair mechanisms. There is a measurable difference between the complex magnetic field emanating from an injured or diseased body part and a normal body part.

It has been recognized in the prior art that the application of a magnetic field to a diseased or injured area of the body can have therapeutic and/or curative effects. Oscillating magnetic fields have been used for years in the course of administering physical therapy to clinic patients suffering from bone fractures. Such devices, known as bone growth stimulators, have proven useful in medical applications to enhance the repair and growth of bone tissue. The device signals, however, are a series of pulses or oscillating waves, which have symmetry typical of electronic-generated signals. More recently, researchers have discovered that the body emits its own complex electromagnetic field pattern. These patterns are associated with some type of stress, or action, such as a bone fracture as well as normal biologic processes. Researchers have theorized since the late 1960's that the information content of a magnetic field waveform is received and recognized by the body (if delivered in a specific manner). It is now believed possible to configure pulsing waveforms and static magnetic fields for an expected biological effect. *Weak Time-Varying and Static Magnetic Fields: From Mechanisms to Therapeutic Applications*, Arthur A. Pilla, Department of Orthopedics, Mount Sinai School of Medicine, New York, N.Y. 10029.

Other studies have also reached this conclusion: "In the past few years a new and fundamentally different approach has been increasingly investigated. This includes the use of magnetic fields (MF), produced by both static (permanent) and time-varied (most commonly, pulsed) magnetic fields (PEMFs). Fields of various strengths and frequencies have been evaluated. There is as yet no gold standard. The fields selected will vary based on experience, confidence, convenience and cost. Since there does not appear to be any major advantage to any one MF application, largely because of the unpredictability of ascertaining the true underlying source of the pain, regardless of the putative pathology, any approach may be used empirically and treatment adjusted based on the response." *Pain Management With Pulsed Electromagnetic Field Treatment (PEMF)*, William Pawluk, Md., MSc Assistant Professor, Johns Hopkins University, School of Medicine, March 2003.

Biologic waveforms have also been associated with specific physical injuries. These waveforms are speculated to have an association with the body's natural healing processes. By capturing these patterns, storing and re-admitting these patterns to the target patient, researchers theorize that the normal "healing process" may be restored more effectively, as the patterns would be natural biologic patterns. The body also emits certain natural biologic waveforms that are associated with the normal health biological function. The natural biologic waveform of the patient target pathology and the patient injury-free target are expected to differ in certain characteristics. In fact, Romanian researchers have reported in the literature that these signals do indeed exist and can be isolated. What is unique about the device described herein is that the unique patterns are used as the delivery content for the therapy session, as opposed to the usual patterns generated in the laboratory. What is described herein is a method of delivering precise magnetic field patterns which agree with the body's own natural magnetic field patterns, and do so with an instrument capable of routine therapy use.

Natural magnetic field waveforms have been discovered associated with biologic processes ever since the development of the SQUID (Superconducting QUantum Interference Device). The SQUID is an extremely sensitive instrument for imaging localized magnetic fields. In conventional techniques for measuring biomagnetic fields, the plane of a detection coil connected to a SQUID is disposed in parallel to the body surface to measure the magnetic field $B_{(x,y,z)}$, as expressed in the Cartesian coordinate system. Results of the biomagnetic field measurement are displayed in the form of a temporal change waveform of the measured field component or an isomagnetic field map (contour map).

Most prior art devices for generating therapeutic magnetic fields do so by energizing a coil with a current signal having a regular pulse rate and symmetrical characteristics, usually a: square wave or a sinusoid. A different approach which involves naturally occurring electrical fields is disclosed in Kraus, U.S. Pat. No. 3,915,151 for "An Apparatus for Promoting Healing Processes," which teaches the use of a function generator for producing current characteristics which are copied from physiological variations in the human body. Kraus therefore recognizes the value of generating therapeutic magnetic fields by replicating naturally occurring electrical signals in the body. However, Krauss refers to replicating the rhythm of mechanical functions, such as the movement of the ribs when breathing, not patterns of localized magnetic fields at a given site on the order of $10^{-7}$ Gauss. Kraus does not teach a process of deriving a refined repair signal for a given injury type to generate a magnetic field based on localized magnetic fields measured from selected test subjects. Notably, the technology to measure such fields was not simply available at the time the Kraus patent issued. Thus, what is lacking in the prior art is a method of using state of the art technology to capture natural magnetic field patterns from the body, and deriving interpolative signals between injured and healthy magnetic field patterns, which can then be directed to injured areas for therapeutic effect. The method of the present invention includes steps of the identifying, extracting, isolating characteristics of magnetic fields emanating from both healthy and injured or diseased portions of the body and then delivering those magnetic field patterns which have a therapeutic effect, and enables the use of natural biologic magnetic field waveforms in the generation and delivery of magnetic fields suit for treatment of a particular injury or disease.

SUMMARY OF THE INVENTION

The method of the invention is a process to capture, store and replicate biologic waveforms which includes the derivation of a Normalizing Signal by interpolating a normal healthy waveform and a Waveform of a diseased or injured person, isolation of the Normalizing Signal, storing of the Normalizing Signal, generation of the Normalizing Signal, delivery of the Normalizing signal, and conformity to a specific treatment protocol.

The discovery process begins with a known pathologic condition. For example, a bone fracture may be the target in question. A bone fracture has well-understood biologic processes at work which serve to repair the injury. These processes all involve the generation and emitting of natural biologic waveforms. The process, therefore, begins with a patient who has a known condition and use of a sensitive measurement device, known as a SQUID (Superconductive QUantum Interference Device), to detect and measure the condition waveforms. The waveforms generated by the body or biologic organisms have certain specific characteristics. The measurement of the natural biologic waveform caused by the underlying pathologic condition is facilitated by the SQUID apparatus, which is routinely used for measuring those types of waveforms.

The isolation process may take place by digitizing the waveforms and performing arithmetical operations thereon. Isolation of the waveforms is a straightforward procedure, by which measurements are taken of a healthy subject and a subject with an injury. Each measurement is captured and digitized using mechanical or electrical conversion means and placed into a common file format.

The procedure to further isolate the subjected natural biologic signal is a process whereby a comparison of the two waveforms yields a "difference" waveform, which is then presented as the suspected biologic waveform contributing to the healing process. The original source waveforms (the "Injury" waveform, and the "Normal" waveform) are used as reference waveforms, in a study to compare the relative effectiveness of those waveforms against the "difference" waveform.

The final selected Normalizing Signal is then stored in electronic form, typically in a digitized fashion, or it may be stored in printed graphical form. This may use a common flat-file or relational database for the electronic storage medium.

The stored electrical signal pattern is then re-generated in a device which then powers an external applicator. Once the basic Normalizing Signal is then re-generated, it is then modulated with respect to frequency, intensity and duty cycle by the generating device. This final signal is then amplified and prepared for delivery to the patient or subject.

Accordingly, it is an objective of the instant invention to provide an apparatus for generating a therapeutic magnetic field, and a novel method for deriving Normalizing signals to be used as a source of the magnetic field.

It is a further objective of the instant invention to utilize magnetic field data taken from biological subjects using the SQUID apparatus to derive a Normalizing Signal which will complement or reinforce the body's own magnetic field in order to accelerate the healing process.

It is yet another objective of the instant invention to provide an apparatus for generating magnetic fields which includes a memory means having a plurality of different Normalizing Signals stored therein.

It is a still a further objective of the instant invention to provide a method for deriving Normalizing Signals for various injuries and ailments and compiling the repair signals into a library.

It is a further objective of the instant invention to provide an apparatus operable to generate a magnetic field having a wave pattern identical to a desired Normalizing Signal by providing a coil with known current/magnetic field characteristics.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

DETAILED DESCRIPTION OF THE INVENTION

Although the invention will be described in terms of a specific embodiment, it will be readily apparent to those skilled in this art that various modifications, rearrangements, and substitutions can be made without departing from the spirit of the invention. The scope of the invention is defined by the claims appended hereto.

Figure 1:
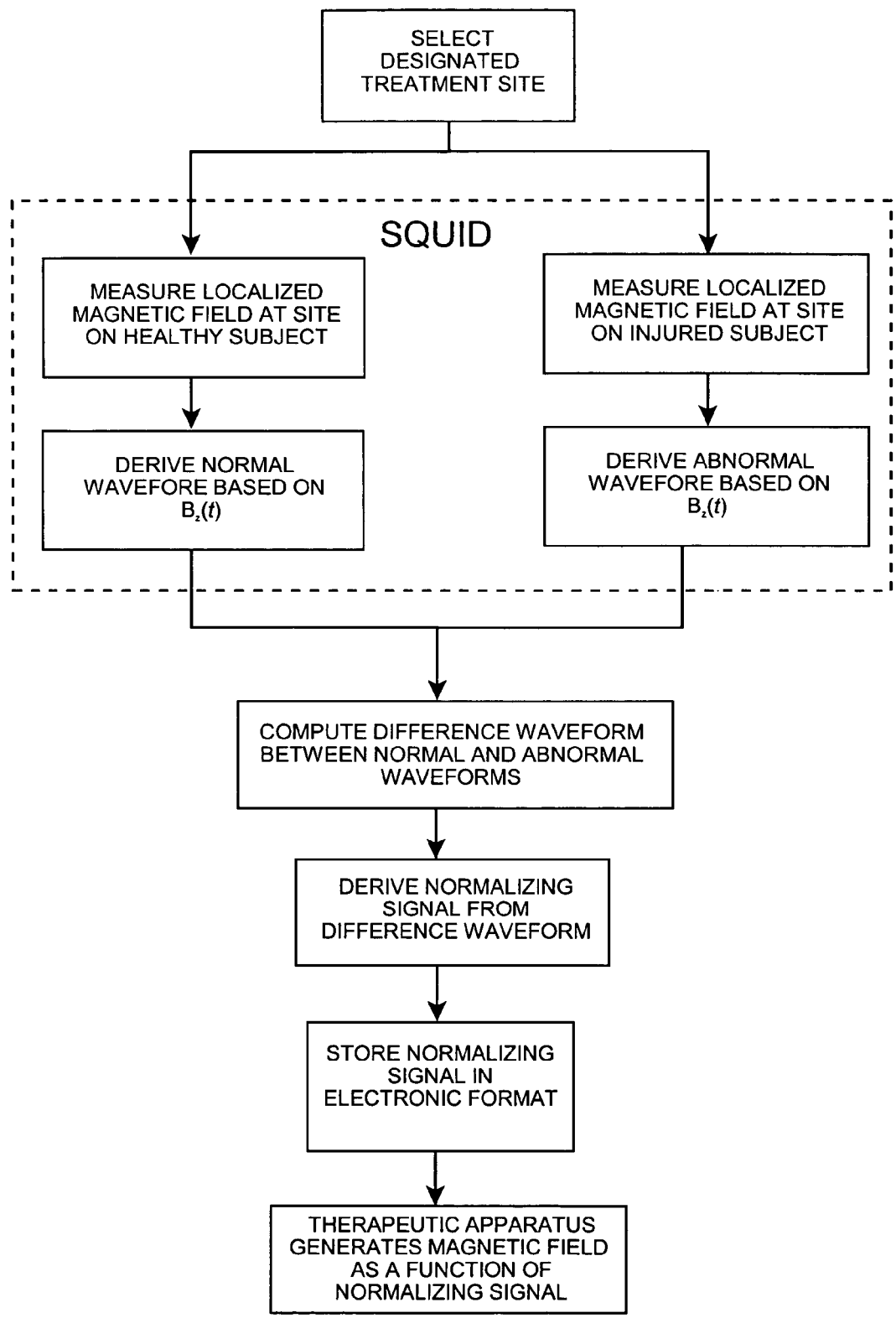
FIG. 1 is a flow chart showing generalized steps for implementation of the method of the invention according to a preferred embodiment.

In one aspect of the instant invention, a method is disclosed for replicating naturally occurring biomagnetic fields, or derivations thereof, for therapeutic application to a living biological subject. Generalized steps for implementation of a preferred embodiment of the inventive method are illustrated in FIG. 1. It will be understood that the illustrated steps in FIG. 1 are broadly depicted for ease of description, and the invention is not limited in this regard.

In the practice of the invention, a database of Normalizing Signals is created which includes a plurality of Normalizing Signals which are each unique for various treatment sites on the body, types of injuries, types of diseases, palliative protocols, etc. The Normalizing Signals are approximations of wave patterns of therapeutic magnetic fields to be applied to a subject at a designated treatment site.

To compile the database of Normalizing Signals, initial measurements are obtained using SQUID magnetometers from test subjects. The operation principles of SQUID magnetometers are well known in the art. A discussion of the SQUID operation principles can be found in Fundamentals of Magnetism and Magnetic Measurements, by Mike McElfrish, Purdue University, ©1994 Quantum Design, the contents of which are herein incorporated by reference.

Figure 2A:
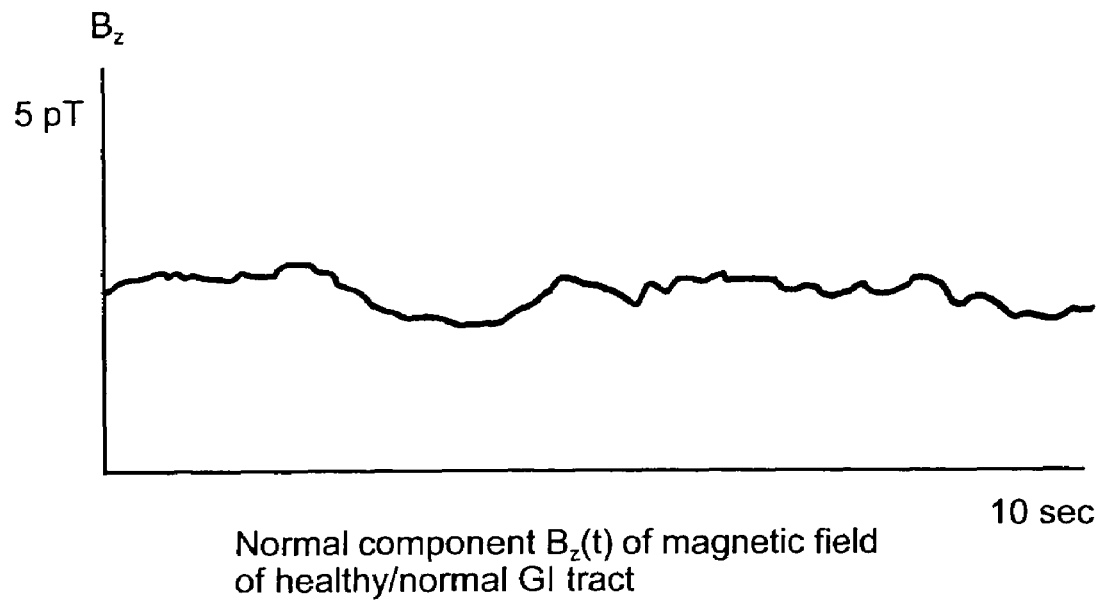
FIG. 2A is an example of measured magnetic waveforms from a Normal subject.
Figure 2B:
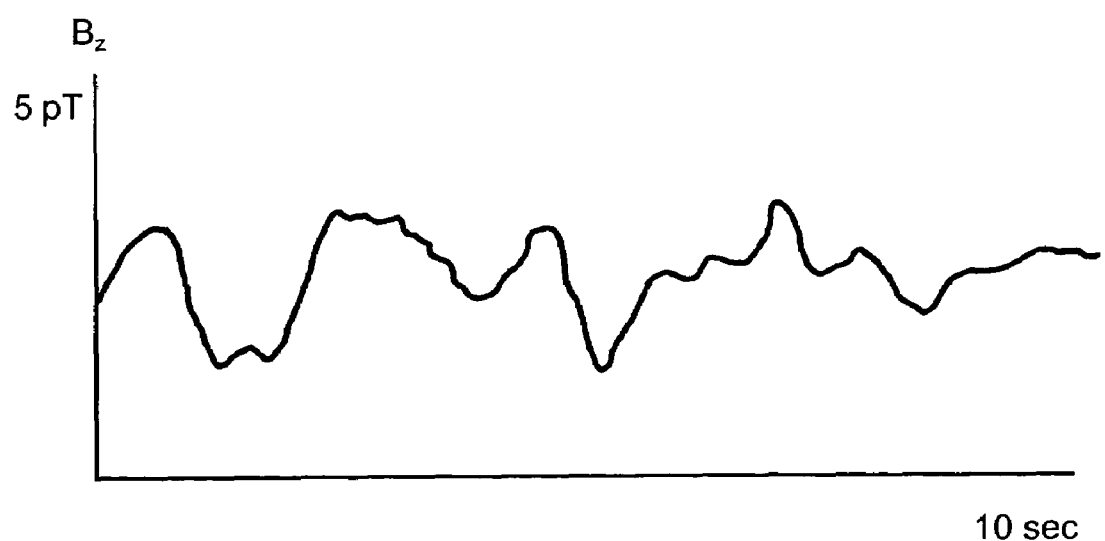
FIG. 2B is an example of measured magnetic waveforms from an Abnormal subject.

The SQUID magnetometers detect the localized magnetic fields and derives the vector components $B_x$, $B_y$, $B_z$ of the magnetic field as function of time over a time t, to produce waveforms such as those shown in FIGS. 2A and 2B. The example waveforms in FIGS. 2A and 2B show the normal component $B_z$ as a function of time. In the harvesting stage, treatment sites are designated and appropriate measurements taken to derive waveforms. It is preferable that measurements be taken from treatment sites categorized as normal, or healthy, and corresponding measurements taken from the same treatment sites injured or diseased sites, which are categorized as abnormal. Magnetic field wave patterns are derived for the same site, i.e. the GI tract, to provide a Normal Waveform (FIG. 2A) and an Abnormal Waveform (FIG. 2B) based on $B_z(t)$ over a period, of time t. In practice, measurements can be taken from different individuals, which may be classified as injured or normal. Measurements can also be taken from the same individual where bodily symmetry allows, for example an injured left arm and a normal right arm on the same individual.

Figure 3:
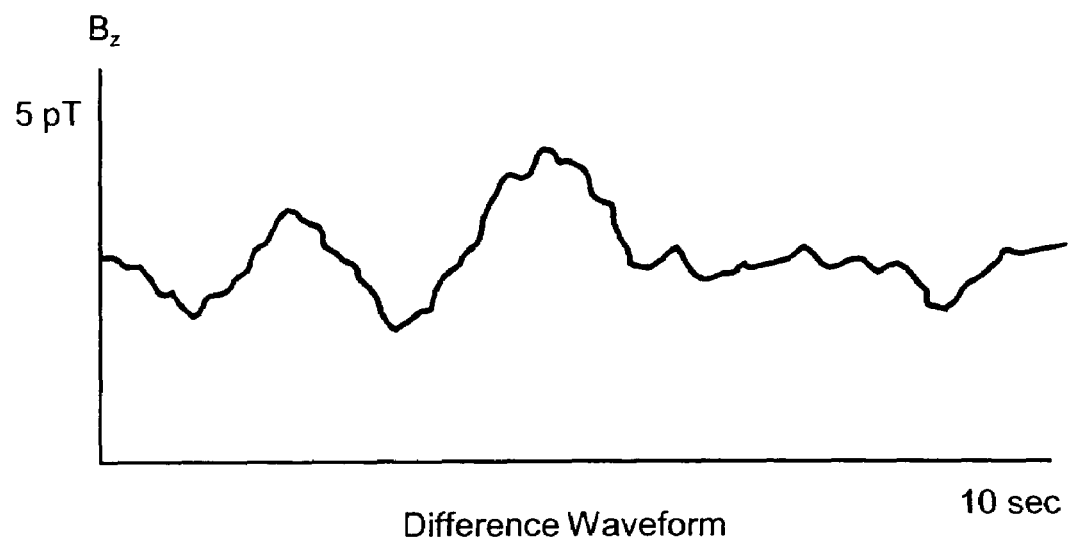
FIG. 3 is an example of a Difference Waveform calculated form the Normal and Abnormal waveforms.
Figure 4:
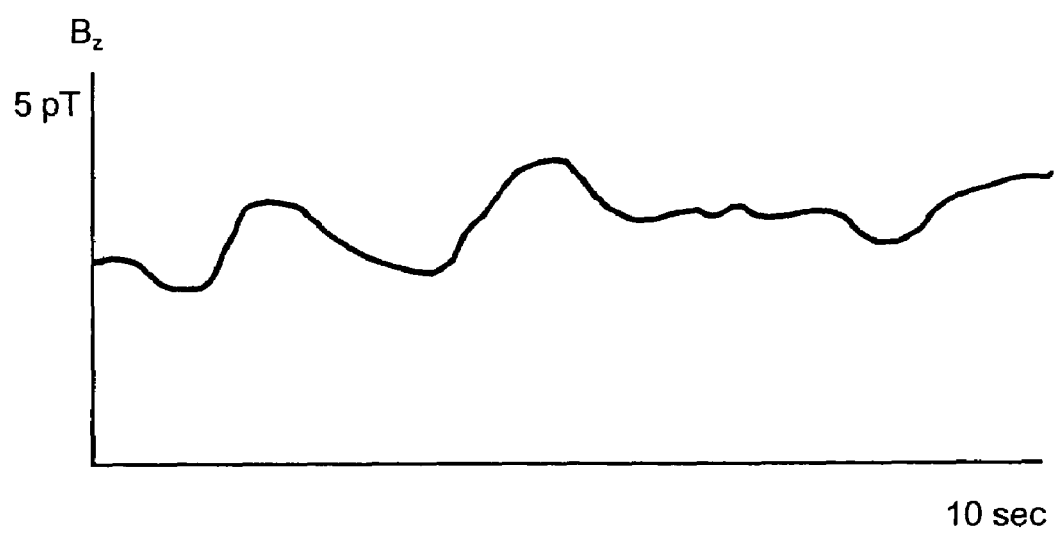
FIG. 4 is an example of a Normalizing Signal derived from the Difference Waveform shown in FIG. 3.

A processing means is provided which is operable to perform arithmetic processing of the healthy waveform and the injury waveform. Using the processing means, a Difference Waveform can be computed from the Normal Waveform and the Abnormal Waveform, which is shown by example in FIG. 3. The therapeutic Normalizing Signal waveform shown in FIG. 4 can then be derived from the Difference Waveform based on predefined treatment algorithms, and can be mathematically manipulated using, for example, dithering techniques and Fourier transforms.

It should be noted that the Normalizing Signal of the invention is not limited to a signal derived from a Difference Waveform. The Normal Waveform itself can be used as the Normalizing Signal if treatment protocols determine that the application of the normal, healthy magnetic field would be therapeutic to speed healing. It is also contemplated that the Abnormal Waveform may be applied directly as the Normalizing Signal in order to reinforce the natural bioelectric healing processes. In another aspect of the invention, the pure unmanipulated Difference Waveform can be used as the Normalizing Signal, to thereby create the normal magnetic field through a directly additive process.

Thus, a plurality of Normalizing Signals can be derived for any number of treatment sites and conditions, or for alternative use at a particular stage of a condition. The plurality of Normalizing Signals are then stored in an electronic format to create a database of Normalizing Signals. The desired Normalizing Signal can be selected for use based on treatment parameters to deliver an appropriate therapeutic magnetic field to the subject.

Figure 5:
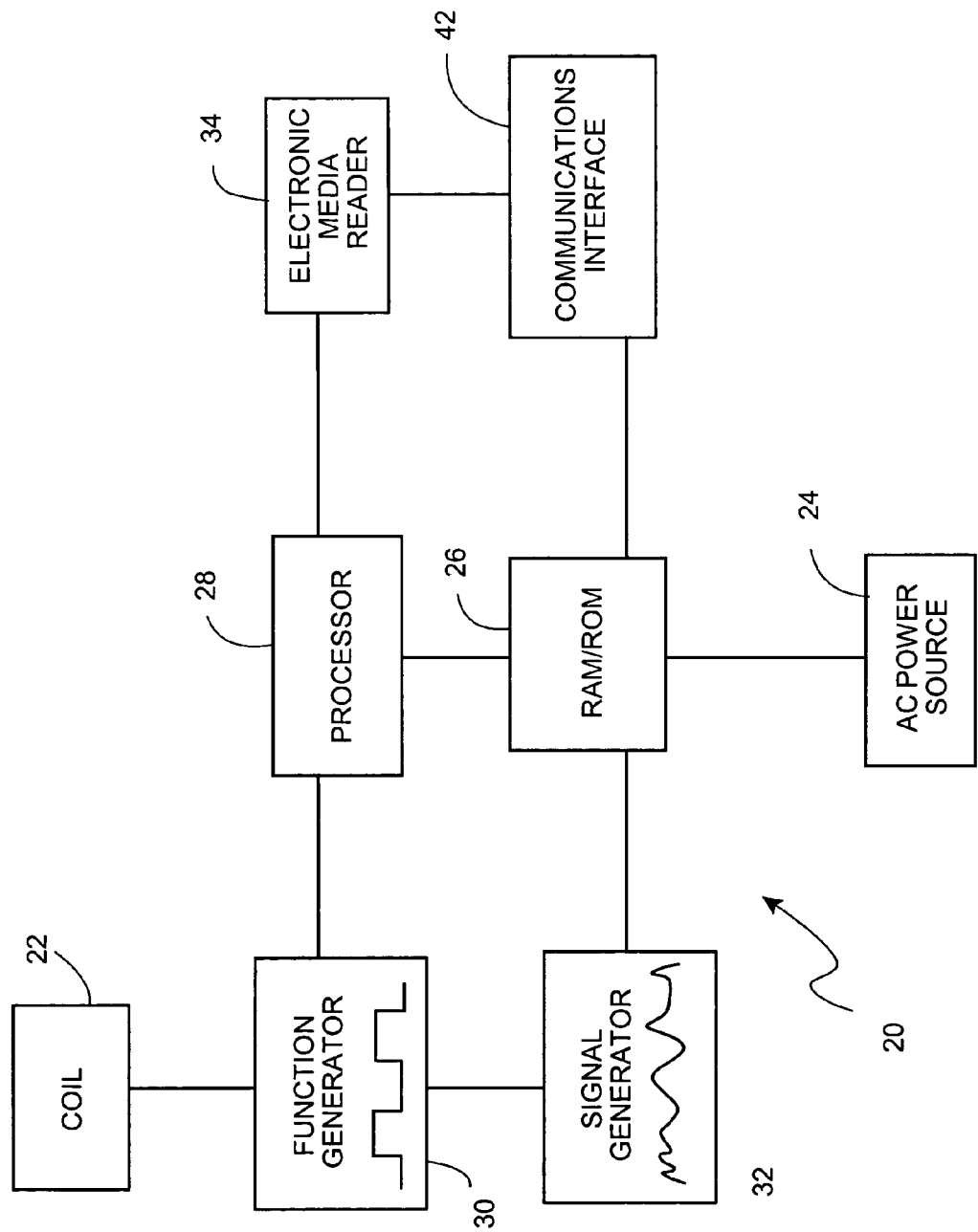
FIG. 5 is a schematic illustration of a therapeutic apparatus for delivering a magnetic field according a preferred embodiment of the present invention.

A therapeutic apparatus 20, schematically illustrated in FIG. 5, is provided to generate the magnetic field for application to a subject. As is the conventional design, the device includes a coil 22 coupled to a current source 24 which causes the coil to produce a corresponding magnetic field. The therapeutic apparatus 20 includes a memory means 26, a processor 28, electronic media reader 34 and a function generator 30 which is coupled to a signal generator 32. The signal generator 32 is operable to generate signals based on stored electronic patterns. The therapeutic apparatus 20 can also include a communications interface 42 which allows the device to be networked in a LAN or WAN.

Figure 6:
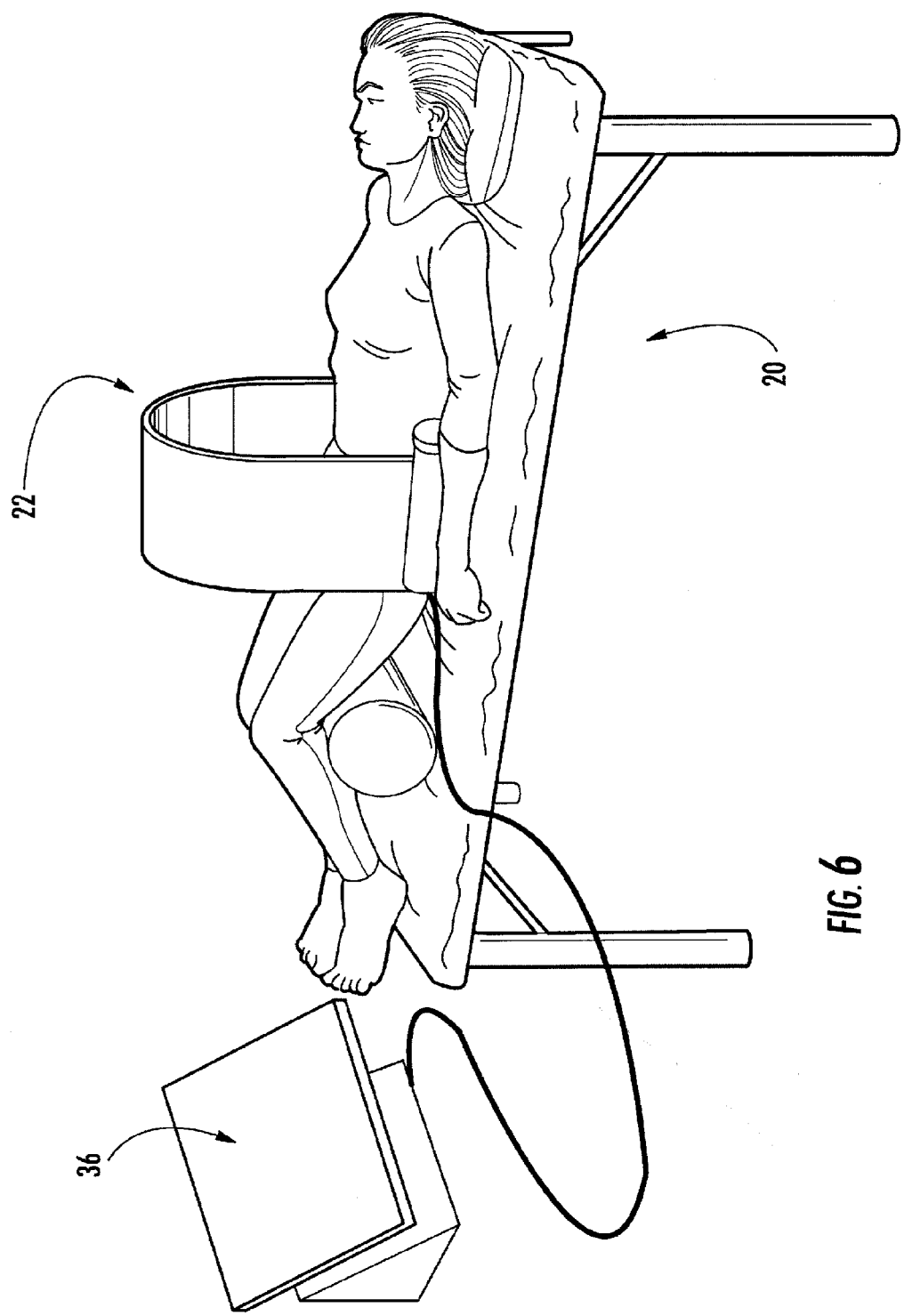
FIG. 6 is a pictorial illustration of the device shown in FIG. 5.

The coil 22 can have any desired configuration as would be ergonomically suitable to deliver the therapeutic magnetic field to a patient. The coil 22 can be toroidal in shape, and sized to receive a portion of the body of the subject patient placed therethrough. A pictorial view of the device 20 is shown in FIG. 6, with a coil 22 sized to encircle the subject's entire body. Coils with a smaller diameter could be used to deliver the field to, for example, a hand or a foot. Other suitable configurations include a planar (or flat) coil or a Helmholtz coil.

The coil 22 has a configuration with known current/magnetic field characteristics with the function of magnetic field with respect to current being defined. In the case of a toroidal coil, the magnetic field can be expressed as $$B = \frac{\mu_0 NI}{2\pi r}$$

where N is the total number of loops on the toroid, and $\mu_0$ is the magnetic permeability constant of the material. The magnetic field therefor varies as a function of the distance from the center of the toroid. In order to generate a measurable time-varying vector component wave pattern approximately equal to the Normalizing Signal, a source current is calculated based on the magnetic field/current characteristics of the coil. In the case of the toroid, the current would be expressed as $$I = \frac{2\pi r B}{\mu_0 N}$$

where B is the value of the magnetic field in pico teslas which is extracted from the selected Normalizing Signal. The Normalizing Signal is repeated as a pulsed pattern, with the frequency, intensity and duty cycle modulated by the function generator 30. The resulting magnetic field has a measurable time-varying vector component wave pattern approximately equal to the Normalizing Signal.

In an alternative embodiment, the Normalizing Signal can be the voltage or current wave pattern required to generate the desired magnetic field vector component wave pattern. In this embodiment, a set of Normalizing Signals would be created for each contemplated coil configuration.

A plurality of Normalizing Signals are stored in an electronic format in a memory means which interfaces with the therapeutic apparatus 20. The therapeutic apparatus includes a means for an operator to select one of the plurality of Normalizing Signals. The database of Normalizing Signals can be stored in the memory 26 of the therapeutic apparatus 20, or alternatively can be stored on portable electronic media such as a CDROM, flash memory card, or portable hard disk drive, with the therapeutic apparatus 20 having the appropriate reader means 34. In the preferred embodiment, the database is store on a CDROM and the therapeutic apparatus 20 includes a CDROM drive.

In real life applications, the Normalizing Signal may need to be adjusted with regard to treatment parameters of the subject, such as age, gender, physical condition, pre-existing ailments, etc. In order to individualize the signal, the therapeutic apparatus 20 can include a means for an operator to input treatment criteria data for a plurality of treatment parameters. The Normalizing Signal can be modulated according to predefined algorithms stored in the memory 26 based on the treatment criteria data. In the illustrated embodiment shown in FIG. 6, a touch screen 36 which displays appropriate menu option is used for data input.

Figure 7:
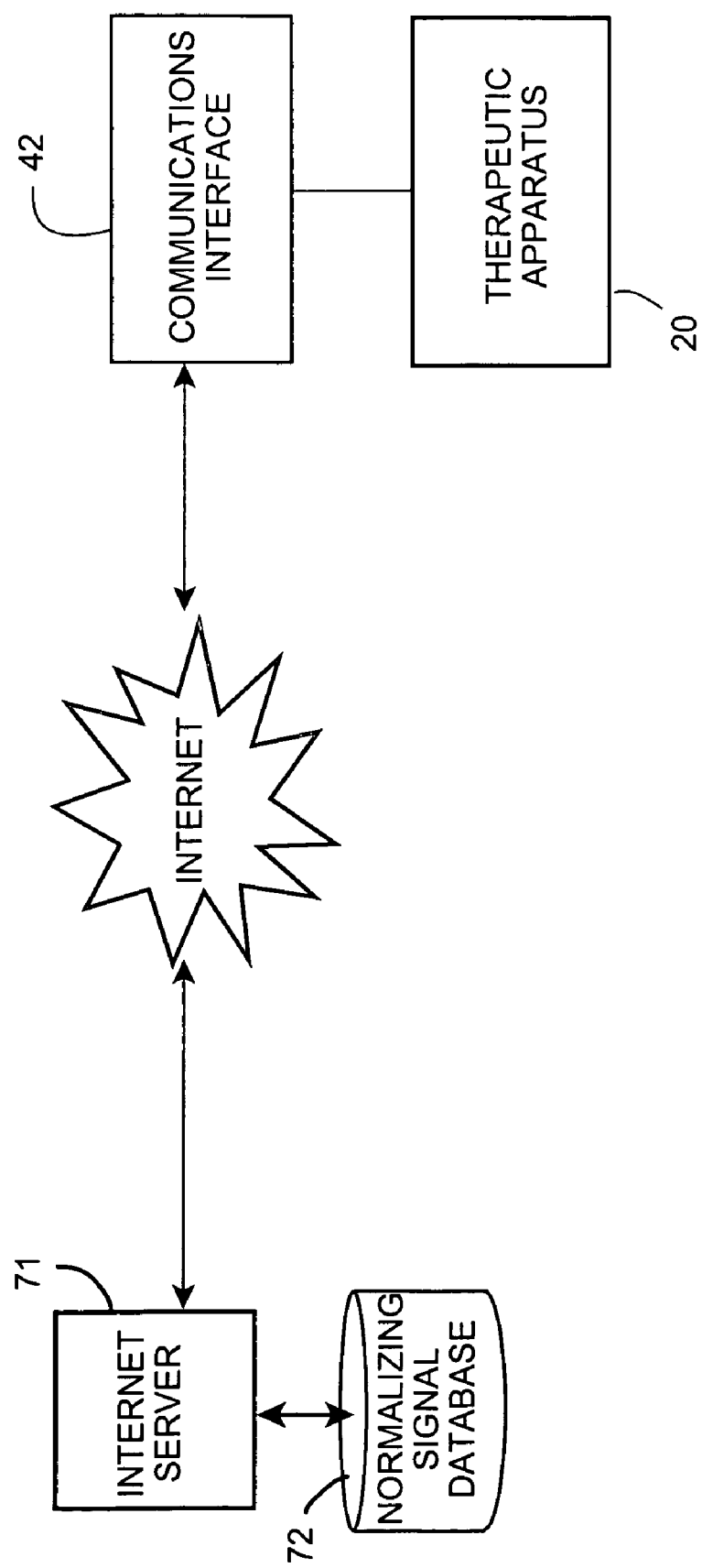
FIG. 7 is a schematic illustration of an alternative embodiment of invention in which Normalizing Signals are downloaded from the Internet.

In another embodiment schematically illustrated in FIG. 7, a plurality of Normalizing Signals are stored on a remotely located Internet server 71, or in a database 72 coupled to the Internet server 71. In this embodiment, the therapeutic apparatus 20 can access the Normalizing Signals over the Internet via communications interface 42. This allows a operator of the to access the server and download the appropriate Normalizing Signal at the time of treatment.

The conformity to a specific protocol may require specifying certain types of stage treatment procedures. These procedures typically require:

Specified administered exposure time to field
Specified time between exposures
Specified number of exposures
Exposure dose (strength of field)
Dose design
Dose duty cycle For example, the administered exposure may require stages exposures of 30, 60 or 90 minute exposures over the course of several days. The exposures may be staged according to a certain delay between each exposure. The dosage may be adjusted up or down according to the needs of the subject. The dose design itself is specified, according to a selection of one or several types of waveforms which are stored in the machine, and the dose may have to be regulated according to a specified duty cycle.

It is to be understood that while a certain form of the invention is illustrated, it is not to be limited to the specific form or arrangement of parts herein described and shown. It will be apparent to those skilled in the art that various changes may be made without departing from the scope of the invention and the invention is not to be considered limited to what is shown and described in the specification and drawings.

I claim:

1. A method for generating a therapeutic magnetic field to be applied to a biological subject which is derived from measured biomagnetic fields, comprising:

harvesting wave patterns from naturally occurring biomagnetic fields wherein the wave patterns are vector components of magnetic fields with respect to time;

deriving a therapeutic Normalizing Signal from the harvested wave patterns wherein the Normalizing Signal is the wave pattern of a therapeutic magnetic field to be applied to a subject;

providing an therapeutic apparatus for generating a magnetic field comprising a coil coupled to a source of current causing the coil to produce a corresponding magnetic field; and generating a therapeutic magnetic field wherein the magnetic field is a function of the Normalizing signal.

2. A method for generating a therapeutic magnetic field to be applied to a biological subject which is derived from measured biomagnetic fields, comprising:

harvesting wave patterns from naturally occurring biomagnetic fields wherein the wave patterns are vector components of magnetic fields with respect to time;

deriving a therapeutic Normalizing Signal from the harvested wave patterns wherein the Normalizing Signal is the wave pattern of a therapeutic magnetic field to be applied to a subject;

providing an therapeutic apparatus for generating a magnetic field comprising a coil coupled to a source of current causing the coil to produce a corresponding magnetic field, the coil having a configuration with known current/magnetic field characteristics wherein the function of magnetic field with respect to current is defined, the apparatus further comprising a memory means, a processing means and a means to generate a source current based on stored electronic signal patterns; and calculating a source current to generate a magnetic field corresponding to the Normalizing Signal based on the magnetic field/current characteristics of the coil wherein the magnetic field has a measurable time-varying vector component wave pattern approximately equal to the Normalizing Signal.

3. The method of claim 2, wherein said step of harvesting wave patterns from naturally occurring biomagnetic fields further comprises the steps of:

providing a magnetometer to detect localized biomagnetic fields at designated site on the subject wherein the magnetometer is operable to detect and measure magnetic field vector components and derive a time-varying wave pattern therefrom;

measuring a localized magnetic field at a designated treatment site on at least one test subject, wherein the designated treatment site on the test subject is categorized as Normal, and deriving a Normal Waveform based on at least one time-varying magnetic field vector component over a period of time t from the healthy test subject.

4. The method of claim 3, wherein said step of harvesting wave patterns from naturally occurring biomagnetic fields further comprises the steps of:

measuring a localized magnetic field at a designated treatment site on at least one test subject, wherein the designated treatment site on the test subject is categorized as Abnormal; and deriving an Abnormal Waveform based on at least one time-varying magnetic field vector component over a period of time t from the healthy test subject.

5. The method of claim 4, wherein said step of deriving a therapeutic Normalizing Signal from the harvested wave patterns further comprises the steps of:

providing a processing means operable to perform arithmetic processing of the healthy waveform and the injury waveform;

computing a Difference Waveform between the Normal Waveform and the Abnormal Waveform; and deriving the therapeutic Normalizing Signal waveform from the Difference Waveform based on predefined treatment algorithms.

6. The method of claim 5, further comprising storing the Normalizing Signal in a memory means in an electronic format.

7. The method of claim 4, further the wherein therapeutic apparatus further includes a means to modulate the Normalizing Signal with respect to frequency, intensity and duty cycle.

8. The method of claim 7, wherein the means to modulate the Normalizing signal is a function generator coupled to the current source.

9. The method of claim 2, wherein the Normalizing Signal is derived for a plurality of designated treatment sites on a living biological subject to provide a plurality of Normalizing Signals corresponding to the plurality of treatments sites and the plurality of Normalizing Signals are stored in an electronic format.

10. The method of claim 9, wherein the plurality of Normalizing Signals are stored in the memory of the therapeutic apparatus in an electronic format, and the therapeutic apparatus includes a means for an operator to select one of the plurality of Normalizing Signals.

11. The method of claim 9, wherein the plurality of Normalizing Signals are stored on portable media in electronic format; and the therapeutic apparatus includes a means to read the electronic media whereby the Normalizing Signals can be generated.

12. The method of claim 11, wherein the portable electronic media is a CDROM, and the means to read the electronic media is a CD ROM drive.

13. The method of claim 11, wherein the portable electronic media is flash memory card; CDROM, and the means to read the electronic media is a flash memory card reader.

14. The method of claim 11, wherein the portable electronic media is a portable hard drive unit which can be coupled to the therapeutic device.

15. The method of claim 11, wherein the therapeutic apparatus includes a means for an operator to select one of the plurality of Normalizing Signals stored on the portable media.

16. The method of claim 2, wherein the therapeutic apparatus includes a means for an operator to input treatment criteria data for a plurality of treatment parameters, and the Normalizing Signal can be modulated according to predefined algorithms based on the treatment criteria data.

17. The method of claim 2, wherein the magnetometer is a superconducting quantum interference device (SQUID).

18. A method for generating a therapeutic magnetic field to be applied to a biological subject which is derived from measured biomagnetic fields, comprising:
    providing a magnetometer to detect localized biomagnetic fields at the designated site on the subject wherein the magnetometer is operable to detect and measure magnetic field vector components and derive a time-varying wave pattern therefrom;
    measuring a localized magnetic field at the designated treatment site on at least one test subject, wherein the designated treatment site on the test subject is categorized as Normal,
    deriving a Normal Waveform based on at least one time-varying magnetic field vector component over a period of time t from the healthy test subject;
    measuring a localized magnetic field at the designated treatment site on at least one test subject, wherein the designated treatment site on the test subject is categorized as Abnormal;
    deriving an Abnormal Waveform based on at least one time-varying magnetic field vector component over a period of time t from the healthy test subject;
    providing a processing means operable to perform arithmetic processing of the healthy waveform and the injury waveform;
    computing a Difference Waveform between the Normal Waveform and the Abnormal Waveform;
    deriving a therapeutic Normalizing Signal waveform from the Difference Waveform based on predefined treatment algorithms;
    providing a therapeutic apparatus operable to generate a localized magnetic field, the therapeutic apparatus including a memory means, a processing means and a means to generate a source current based on stored electronic signal patterns;
    storing the Normalizing Signal in the memory means in an electronic format; and
    generating a magnetic field from the therapeutic apparatus directed to the designated treatment site on a subject wherein the magnetic field is function of the Normalizing Signal waveform.

19. The method of claim 18, wherein the therapeutic apparatus comprises a coil adapted to be applied to the designated treatment site which is coupled to a source of current causing the coil to produce a corresponding magnetic field, the coil having a configuration with known current/magnetic field characteristics wherein the function of magnetic field with respect to current is defined.

20. The method of claim 19, wherein said step of generating a magnetic field further comprises the step of calculating a source current to generate a magnetic field corresponding to the Normalizing Signal based on the magnetic field/current characteristics of the coil wherein the magnetic field has a measurable time-varying vector component wave pattern approximately equal to the Normalizing Signal.

21. The method of claim 18, wherein the therapeutic apparatus includes an electrical function generator coupled to the AC current source.

22. The method of claim 21, further wherein the function generator is operable to modulate the Normalizing Signal with respect to frequency, intensity and duty cycle.

23. The method of claim 18, wherein the Normalizing Signal is derived for a plurality of designated treatment sites to provide a plurality of Normalizing Signals which correspond to the plurality of sites, and said Normalizing signals are stored in an electronic format.

24. The method of claim 23, wherein the plurality of Normalizing Signals are stored in the memory of the therapeutic apparatus in electronic format, and the therapeutic apparatus includes a means for an operator to select a desired Normalizing Signal.

25. The method of claim 23, wherein the plurality of Normalizing Signals are stored on portable media in electronic format; and the therapeutic apparatus includes a means to read the electronic media whereby the Normalizing Signals can be generated.

26. The method of claim 23, wherein the portable electronic media is a CDROM, and the means to read the electronic media is a CDROM drive.

27. The method of claim 25, wherein the therapeutic apparatus includes a means for an operator to select a desired Normalizing Signal stored on the portable media.

28. The method of claim 18, wherein the therapeutic apparatus includes a means for an operator to input treatment criteria data for a plurality of treatment parameters, and the Normalizing Signal can be modulated according to predefined algorithms based on the treatment criteria data.

29. The method of claim 18, wherein the magnetometer is a superconducting quantum interference device (SQUID).

30. The method of claim 18, wherein the therapeutic apparatus further comprises a communications interface.

31. The method of claim 30, wherein the Normalizing Signals are stored in electronic format in remote server having a communications interface, and the method further comprises the steps of:
    coupling the communications interface to the remote server for bidirectional data transfer;
    selecting a Normalizing Signal residing on the remote server; and
    downloading the selected Normalizing Signal.

* * * * *